United States Patent [19]

Silvetti

[11] 4,414,202

[45] Nov. 8, 1983

[54] COMPOSITION FOR TREATMENT OF WOUNDS

[76] Inventor: Anthony N. Silvetti, 930 Ashland Ave., River Forest, Ill. 60305

[21] Appl. No.: 301,472

[22] Filed: Sep. 14, 1981

Related U.S. Application Data

[63] Continuation of Ser. No. 117,717, Feb. 19, 1980, abandoned.

[51] Int. Cl.³ .................. A61K 31/70; A61K 33/26
[52] U.S. Cl. .................................. 424/147; 424/180; 424/319; 424/DIG. 13
[58] Field of Search ................. 424/180, 319, 147

[56] References Cited

U.S. PATENT DOCUMENTS 3,812,252  5/1974  Silvetti .................. 424/180
4,105,783  8/1978  Yu et al. ................ 426/283

FOREIGN PATENT DOCUMENTS 7513892  11/1975  Netherlands ............ 424/280

OTHER PUBLICATIONS

Chemical Abstracts 92:4024h, 1980 (McKeehan et al.).
The Merck Index, 9th ed., 1976, p. 695.
American Drug Index, 1975, p. 228.
Biddle's Materia Medica & Therapeutics, p. 431, 1895.
Chemical Abstracts 80:13050t (1974) (Walser).
Br. J. of Surgery, vol. 63, pp. 427–430, 1976, Viljanto et al.
Methods of Tissue Culture, 3rd Ed. (1962), Hoeber Med. Div., Harper & Rowe, Parker, pp. 53–61.

*Primary Examiner*—Leonard Schenkman
*Attorney, Agent, or Firm*—Silverman, Cass & Singer

[57] ABSTRACT

Treatment of skin wounds with starch hydrolysate composition can be improved by irrigating the wound with a buffered salt solution having a pH in the range of approximately 6–7.8 prior to application of the starch hydrolysate composition. Additionally, the treatment can include further irrigation with amino acid solution. A preferred starch hydrolysate composition is compounded to include alphaketoglutaric acid or a salt thereof.

6 Claims, No Drawings

COMPOSITION FOR TREATMENT OF WOUNDS

This is a continuation of application Ser. No. 117,717 filed Feb. 19, 1980 now abandoned.

BACKGROUND OF THE INVENTION

In current medical practice, wounds and ulcers are usually irrigated and washed with either tap water, sterile distilled water or sterile normal saline solution, which is generally made isotonic with human plasma by concentration of primarily sodium chloride at a level of approximately 0.9 weight percent and with solution pH of less than about 6. It has now been learned that while such normal saline solution is an effective bacteriostatic/bactericidal agent, such solution can be a long-run detriment to the well-being of the tissue cells because they slow down or prevent healing of the wound.

As described in U.S. Pat. No. 3,812,252 which is incorporated by reference herein, a particularly effective healing treatment for wounds and skin defects such as burns, ulcers and leisions is the application of a medicinal dressing containing as an essential ingredient starch hydrolysate having Dextrose Equivalent of less than about 35. In such wound treatment the starch hydrolysate produces the formation of a film which is intimately adhered to the underlying granulation tissue and which is semipermeable to gas and fluids and provides an ideal protective cover that will reduce fluid and plasma losses and invasion by pathogenic bacteria. In addition, it appears that the starch hydrolysate provides a topical or local hyperalimentation, that is local nutrition, providing a gradual release of glucose which is particularly effective in nutrition of tissue, both damaged and nascent, which have become relatively isolated from normal blood flow nutrition. The cessation of blood flow to such an ischemic leision can be developed in a slow and gradual form such as in the case of decubitius ulcers and statis ulcers, or may take place more acutely such as in thermo-radiation and chemical burns. In the absence of nutrition such as provided by the treatment with starch hydrolysate, the decrease in the rate of fluid delivery of nutrients brings a progressive impairment in the viability of cells and tissues which eventually leads to degeneration and death of the tissue and cells in a condition known as necrosis which is generally accompanied by bacterial, fungal, and/or viral contamination and proliferation. As further pointed out in the aforementioned patent, treatment of exudative skin wounds with a starch hydrolysate dressing produces a greatly reduced bacteria count of an infected wound and inhibits infection of an uninfected wound. In addition, application of the starch hydrolysate to a wound or ulcer produces a film or semi-permeable membrane which allows edemic liquid to pass through while protinaceous material is retained within the body, allowing reduction in the volume of exudate in relatively clean condition. In addition, the patent teaches nutritive agents, such as the amino acids, cystine and cysteine, and vitamins such as ascorbic acid (vitamin C) may also be mixed or applied along with particulate starch hydrolysate to promote the formation and growth of healthy granulation tissue.

In accordance with this invention, improvements in the starch hydrolysate treatment of wounds have been developed to provide irrigative treatment of the wound, effective to promote the healing process, as well as beneficial compounding of the starch hydrolysate material.

SUMMARY OF THE INVENTION

In the treatment of wounds and skin defects such as pressure ulcers, response to the application of starch hydrolysate dressing can be improved by prior irrigation of the wound with a buffered salt solution maintaining a pH in the range of approximately 6-7.8. When the wound is daily irrigated particularly with balanced salt solution buffered with phosphate to a pH of about 7.4 and covered with a starch hydrolysate, buffered salt solution not only disinfects the wound but also promotes formation of healing granulation tissue. In a preferred formulation, the buffered salt solution contains dissolved ferrous salt as a promoter for collagen formation. Additionally the buffered salt solution can contain an amino acid component and separate irrigation of the wound with amino acid solution either before or after application of the starch hydrolysate accelerates the wound healing process.

Compounding the starch hydrolysate composition to contain alphaketoglutaric acid, in addition to ascorbic acid or ascorbate salt, can provide a component which appears to be essential for activation of the tissue enzyme, protocollagenhyrdoxylase for collagen formation.

DETAILED DESCRIPTION OF THE INVENTION

In the development of treatment for burns and other exudative wounds and leisons, layered petralatum and gelatious protein films have been used for sealing of the wounds to prevent serious loss of body fluid. Unfortunately, formation of excessively soft moist tissue under such applied seals has not only hampered attempted autograft and homograft skin transplant but in addition, such tissue has encouraged growth of secondary infections. Consequent disinfectant cleansing of the wounds typically with normal saline solution requires replacement of such dressing daily resulting in rupture of the fragile granulation cells.

Treatment of skin wounds with starch hydrolysate having a low Dextrose Equivalent (D.E.) has now been improved according to this invention in the preparation of the wound for application of the starch hydrolysate by irrigation with a disenfectant balanced salt solution which is buffered to maintain a pH of the solution within the range of approximately 6 to 7.8 with hydrogen phosphates or bicarbonates. A suitable buffered salt solution for use in wound treatment with starch hydrolysate is now commercially available from Baxter Laboratories under the trade name TIS-U-SOL ® which was originally formulated for ear surgery procedures to reduce the scar tissue usually obtained when normal saline was employed. While TIS-U-SOL is buffered with sodium and potassium hydro-phosphates to maintain a pH of approximately 6, it is preferred that the balanced salt solution employed for disinfectant irrigation according to this invention, have a pH maintained in the range of 7.2-7.6, most preferably about 7.4, such as the phosphate-buffered salt solution known as Dulbecco's solution. Preparation of Dulbecco's solution and similar buffered stock solutions are described by Raymond C. Parker in "METHODS OF TISSUE CULTURE" 3rd Edition (1962) pp. 58-59. Compositions of TIS-U-SOL and Dulbecco's solution are presented in Table I together with two additional buffered salt solution designated A and B. Solution A is parcticularly preferred for irrigation in the method of this invention because it contains dissolved ferrous salt, FeSO₄, providing Fe++ ion in the solution which is believed to promote the healing formation of collagen in granulation and connective tissue. Other suitable ferrous salts such as $FeCl_2$ and ferrous gluconate can also be employed.

TABLE I

| | Buffered Salt Solution Preparations (grams per aqueous liter) | | | |
|---|---|---|---|---|
| | TIS-U-SOL | Dulbecco's Solution | Solution A | Solution B |
| pH | 6 | 7.4 | 7.4 | 7.4 |
| Component | | | | |
| NaCl | 8 | 8 | 8 | 8 |
| K Cl | 0.4 | 0.20 | 0.4 | 0.4 |
| Ca Cl₂ | — | 0.1 | 0.2 | 0.2 |
| Mg Cl₂ 6H₂O | — | 0.1 | — | — |
| Mg SO₄ | 0.2 | — | 0.2 | 0.2 |
| Na₂ HPO₄ | 0.0875 | 1.15 | 1.15 | 1.15 |
| KH₂ PO₄ | 0.0625 | 0.2 | 0.2 | 0.2 |
| Dextrose | 1 | — | — | — |
| Glucose | — | — | 1.0 | 1.0 |
| Zn Cl₂ | | | 0.001 | — |
| Fe SO₄ | | | 0.001 | — |

These balanced salt solutions generally containing chlorides of sodium, potassium, and calcium and particularly those buffered to a pH of approximately 7.4, have been found to be very effective in the preparation of wounds and granulation tissue for the application of starch hydrolysate dressing. A typical pressure syringe can be employed for pressure irrigation of the exudative wound with the buffered salt solution achieving both disinfection of the wound and promotion of its healing in contrast to use of normal saline solution.

Starch hydrolysate having a Dextrose Equivalent (DE) less than about 35 suitable for application to the wound in the treatment according to this invention can be prepared generally by subjecting gelatinous starch to the hydrolytic action of an acid or enzyme as more fully described in U.S. Pat. No. 3,812,252 and U.S. Pat. No. 3,849,194, which patents are incorporated by reference herein. The starch hydrolysate material can be applied to the wound as a particulate material such as a powder, or as material such as a gel, paste, dispersion, solution or syrup. Preferably, the starch hydrolysate is applied in powder form which is commercially available from Corn Products Company under the trade name MOR-REX ™ typically in product grade designated Mor-Rex 1918 having a DE of approximately 10–13 and average molecular weight of approximately 2000 and Mor-Rex 1908 having average molecular weight of about 4,000. Both such products are representative of starch hydrolysate materials within the preferred DE range of approximately 5–25.

Typically, the starch hydrolysate is gamma radiated for sterilization; however, it has been found that unradiated starch hydrolysate material may produce even greater healing results without radiation oxidation of the free hydroxl groups on the polysaccharide chain which are believed to be effective in bacterial defense. Consequently, dry heat sterilization of the starch hydrolysate material can provide improved wound healing.

As described in the aforementioned U.S. Pat. No. 3,812,252, the wound treatment can include ascorbic acid in admixture or application along with the starch hydrolysate material to promote the formation and growth of healthy granulation tissue. Ascorbate salts such as those of sodium, potassium and calcium can also be employed, though ascorbic acid is a preferred component for blending with the starch hydrolysate powder at a level in the range of approximately 0.5–20 weight percent of the blended composition, preferably about 5–7.5 weight percent corresponding to a weight ratio of approximately 20 parts starch hydrolysate to one part ascorbic acid or ascorbate salt. While ascorbic acid appears somewhat more effective than the ascorbate salts and is less readily oxidized, mixtures of ascorbic acid and ascorbate salt can also be employed in order to reduce acidity.

Generally, in the preparation of wounds for treatment with starch hydrolysate dressing, the patient selected for study is carefully examined, test areas photographed, and when possible the volume of the leison measured. Biopsy, planometric, bacterial culture, and sensitivity studies are made and thereafter the ulcer or wound is carefully, surgically debrided with all necrotic tissue removed mechanically. Where necessary, a water pulsating instrument, such as one of the instruments available under the trade name Water Pik, has been found to facilitate the debridment of necrotic tissues and serves the purposes of saving tissues that may be viable. Enzymatic debridment can also be carried out when necessary, usually employing proteolytic enzymes such as Travase, Biozyme, collagenase, and Elase.

When the lesions are grossly infected or contaminated, treatment for a few days (one up to 3-4 days) with topical antibacterial agents, can be employed particularly when Gram-Negative organisms are present, such as Pseudomonas Aeruginosa and E. Coli; suitable agents include silver nitrate (0.1%–0.5%) solution and Silver-Sulfadiazine cream (Silvadane ®, Sulfamylon ®).

Broadly, the treatment procedure in accordance with this invention begins with irrigation of the wound with the buffered salt solution, typically employing a syringe for pressure irrigation. Thereafter, the wound is covered with the starch hydrolysate composition preferably containing both ascorbic acid and alphaketoglutaric acid. The initial application of the starch hydrolysate material should be sufficient in amount to allow formation of a film over the entire area of the wound. A perforated non-adhering dressing (of the TELFA ® type) can be applied over the treated wound to allow removal of the dressing for daily repeating the foregoing treatment. Preferably, further irrigation of the wound is carried out by slight moisturization of the TELFA dressing with a minimal amount of amino acid solution as described hereinafter. A roller bandage may then be applied.

The following examples illustrate the treatment in accordance with the method of this invention but do not indicate limitation upon the scope of the claims.

EXAMPLE 1

A 60 year old obese widow had large bilateral skin ulcers due to venous stasis of twelve years duration. Both ulcers were grossly infected with abundant purulent, foulsmelling exudate. There were at least 4 bacterial species present: Klebsiella Pneumoniae, Pseudomonas aeroginosa, Enterococci, Proteus Mirabilis, Staphicococcu Aureus, Coagulase positive. The patient was placed on a modified protein sparing diet and was asked to keep her legs elevated at 20° as much as possible. Culture and sensitivity studies were carried out and were as follows: Upon admission and for 3 days the ulcers were treated with 0.5% Silver Nitrate soaks. Treatment consisted in daily inspection and thorough washing with sterile Dulbecco's phosphate buffered solution and subsequent application of a thin layer of sterile MOR-REX 1918 starch hydrolysate powder blended with approximately 5% ascorbic acid. The ulcer site was then covered with non-adhering dressing (Telfa ®) and the legs were bandaged with Kerlex roller bandage. As early as 48 hours following the initiation of treatment, it was observed that the granulation tissue became bright red and highly vascularized and the amount of purulent exudate began to decrease. The previously described four odor had disappeared by the 3rd day of treatment. By the seventh day of treatment, the epithelium was seen proliferating in the periphery of the ulcer in a centripetal manner. By the 12th post-treatment day the epithelium had advanced to cover about 30% of the original ulcer site. The granulation tissue continued to grow and show a high degree of micro-vascularization and absence of infection and purulent exudate. By the 43rd post-treatment day leg ulcers were totally and completely covered by smooth, scar free, newly grown skin and the patient was discharged. Two and a half years later the ulcers have not reoccured.

EXAMPLE 2

A 74 year old man, affected with late onset diabetes mellitus poorly controlled with insulin, had an infection of his right foot and developed gangrene of his right fifth toe which required trans-metatarsal amputation at the level of the 5th metatarsal bone with extensive debridment of the dorsal and planar aspects of the foot. A grossly infected, foul smelling post-operative wound with exposure of multiple necrotic tendons and bones was present at the time of initiation of treatment.

The following bacterial species were present: Pseudomonas Aeruginosa, Staphilococcus aureus (coagulase positive) and Proteus Mirabilis. Treatment consisted in daily irrigation with Dulbecco's solution and application of powdered starch hydrolysate with approximately 5 wt. % added ascorbic acid. The wound was covered with a non-adherent dressing (Telfa ®). Minimal surgical debridment, mostly of necrotic tendons was carried out at the bedside. Pulsating water-jet debridment, mostly of necrotic tendons was carried out at the bedside. Pulsating water-jet debridment was also carried out at the bedside on several occassions using Dulbecco's solution in a Water Pik ® instrument.

Infection subsided by the end of the 5th post-treatment day. The wound was filled by rapidly growing, highly vascularized granulation tissue which surrounded and covered the exposed bone and joint structures, as well as viable tendons. Several deep and wide tissue gaps were reconstructed by the described granulation tissue. The peripheral epithelium was seen to proliferate, starting on the 5th post-treatment day. By the 19th post-treatment day the post-amputation area had been filed by smooth, highly vascularized granulation tissue with absence of local manifestations of infection.

Epithelium was clearly seen growing in a centripetal manner from the edges of the wound. By the end of the 44th post-treatment day the original post-amputation defect had decreased in size strikingly, measuring only 1.4×2 cms. Because of administrative considerations, it was decided to autograft the remaining wound area. This was successfully accomplished and the patient left the hospital fully ambulatory.

EXAMPLE 3

A 28 year old paraplegic widow affected with a pre-sacral deep decubitus ulcer of three years standing. The patient became paraplegic when a bullet transected her spinal cord at the level of the second thoracic vertebra. At the time of admission to our service the decubitus ulcer measured approximately $2\frac{1}{2} \times 1\frac{1}{2}$ inches, the surface of the sacrum could be seen and there was an abundant, foul smelling purulent exudate. Cultures and sensitivity were taken. There were at least 3 bacterial speciies present. Treatment consisted in daily irrigation with sterile Dulbecco's solution and application of sterile starch hydrolysate powder with approximately 5 wt. % added sodium ascorbate. On the first post-treatment day the purulent exudate was replaced by a syrup like, odorless brownish discharge. Proliferation of a highly vascularized granulation tissue, forming at the bottom of the ulcer, over the sacrum, could be seen from the 2nd post-treatment day. The peripheral epithelium began to grow in a centripetal manner. By the 32nd day the granulation tissue had grown well above the skin edges and the ulcer was completely closed on the 45th day. No scar tissue or contractures were noted in this case.

EXAMPLE 4

The subject was a 76 year old bedridden unmarried woman with a deep 5th degree decubitus ulcer of the pre-sacral area of eighteen years duration (18 years). The pateint was paralyzed because of successive extensive cerebro-vascular accidents (strokes) and had progressive brain atrophy. Her decubitus ulcer was of an ischemic nature due to infection and pressure. It had an oval shape and measured at the start 12×8.5 cms. Its depth extended down to the bone plane. The ulcer was covered by abundant necrotic tissue and foul smelling, purulent exudate. It was initially treated with daily irrigation with phosphate buffered salt solution and starch hydrolysate and as of the first and second day the infection became under control and granulation tissue begam to grow in the periphery of the ulcer, but not at the bottom, over the sacral bone. After 3 weeks of treatment with starch hydrolysate and with very little centripetal growth seen, a new preparation of starch hydrolysate with 5% sodium ascorbate was applied on a daily basis, following daily irrigation with phosphate buffered salt solution. It was then observed that the rate of healing increased in a striking and significant manner. Both granulation tissue growth and epidermal growth and contracture increased significantly against the effect obtained with starch hydrolysate alone. The bottom of the ulcer began to be covered by a much more abundant and vascularized granulation tissue and the advancement of epithelium became more remarkably. By the end of 8 weeks the original skin defect was practically closed, except for a central area measuring 1×2 cms which was finally covered with autologous skin graft.

This case is extremely interesting because the condition of the patient was extremely poor. She was 76 years old, unable to feed hereself and was senile, cachectic with progressive brain atrophy and bilateral paralysis due to previous multiple strokes. She responded well, initially, to the treatment with phosphate buffered salt solution, but by three weeks the growth of granulation tissue became stagnant. When sodium ascorbate was added to the starch hydrolysate the rate of production of granulation tissue and closure of the edges of the ulcer increased about double.

Further improvement of wound healing in the treatment of this invention has been obtained by employing an amino acid solution to further irrigate the wound area either before or after application of the starch hydrolysate dressing. The amino acid compositions need not include cystine or cystein as suggested for promotion of healthy granulation tissue in the aforementioned U.S. Pat. No. 3,812,252. It has been found that when treating the wounds and ulcers with a multiple amino acid solution, after only 24 hours post-operative or less, the thin shiny film produced by the starch hydrolysate remained attached to the underlying tissues of the wound even when detaching the dressings. Surprisingly the film formed upon such additional irrigation with amino acid solution proved to be slightly soluble in water or saline solution whereas its solubility in TIS-U-SOL ® is insignificant.

In a recent paper published in the British Journal of Surgery, Vol. 63 (1976) pp. 427-430, entitled "Local Hyperalimentation of Wounds", Viljanto and Raekallio report the use of viscose cellulose sponge as a temporary cover for deep burns. In the effort to promote local cellular hyperalimentation of the wounds, the sponge was moistened by continuous slow infusion of amino acid/vitamin solutions additionally containing low levels of glucose and ascorbic acid. They report a more active granulation tissue and the disappearance of infection in the wounds so treated. Unlike the actual healing of the lesions accomplished by the starch hydrolysate treatment according to this invention, the temporary sponge cover for the wound was removed for skin grafting of the granulation surfaces.

In accordance with the treatment of this invention, natural or synthetic amino-acid can also be added to the buffered salt solution employed for irrigation of the wound. Moreover, it has been found that improved healing can be obtained by irrigating the wound with an aqueous solution of as little as 10 weight percent amino acids which is commercially available in preparations designed for intravenous use such as those available from Baxter Laboratories and Abbott Laboratories. One such amino acid solution is supplied by Abbott Laboratories under the tradename AMINOSYN TM in the form of approximately 10 weight percent total amino acid concentration with the nominal composition presented in Table II as follows:

TABLE II

AMINOSYN TM 10% Amino Acid Solution
Composition in mg/100 cc of solution (ph 5.3)

| Physiological essential amino acids | |
|---|---|
| L-Isoleucine | 720 |
| L-leucine | 940 |
| L-Lysine | 720 |
| L-Methionine | 400 |
| L-Phenylalanine | 440 |
| L-Threonine | 520 |
| L-Tryptophane | 160 |
| L-Valine | 800 |

| Physiological non essential amino acids | |
|---|---|
| L-Tyrosine | 44 |
| L-Alanine | 1280 |
| L-Arginine | 980 |
| Glycine | 1280 |
| L-Proline | 860 |
| L-Histidine | 300 |
| L-Serine | 420 |

TABLE II-continued

AMINOSYN TM 10% Amino Acid Solution
Composition in mg/100 cc of solution (ph 5.3)

| Total amino acids | 10g/100 cc of solution |
|---|---|

To this 60 mgs. of Potassium metabisulfite as a preservative are added.

Suitable variations in the composition of the amino acid solution presented in Table II can be made for use in the treatment according to this invention, however it is preferred that not less than about 10 weight percent total amino acid concentration be employed in order to minimize amino acid loss in the irrigation as well as to reduce dislogement of starch hydrolysate applied to the wound prior to irrigation with the amino acid solution. An original 10 weight percent amino acid solution cen be concentrated by boiling in a vacuum to a 20 weight percent, 30 weight percent, 40 weight percent and 50 weight percent or higher concentration of the amino acids for suitable irrigation. In addition to selection of one or more of the amino acids presented in Table II, asparagine, aspartic acid, cystein, glutamine and glutamic acid can be added for example to the Aminosyn TM formulation preferably at a level of approximately 10-15 mg. of each of the one or more additional amino acids per 100 cc of solution.

It has also been found in accordance with the treatment of this invention that particulate amino acid, typically in crystalline form, can be blended with the starch hydrolysate powder applied to the wound; suitably, the amino acid concentration in such blend can be in a range of approximately 10-30 parts by weight starch hydrolysate for each part by weight total amino acid and it has been found that total amino acid concentration of approximately 5 weight percent of the blended composition is effective in promoting the healing of the wound. In a particularly preferred formulation, glycine, L-proline, and L-Lysine are blended with the starch hydrolysate powder in order to provide a composition for application to the wound which directly combines the starch hydrolysate with the three amino acids which are believed to be most essential to the formation of collagen, the principal molecular component of both granulation tissue and connective tissue. Preferably, at least one of the foregoing group of three amino acids is blended with the starch hydrolysate in relative concentration of approximately 10-30 parts by weights starch hydrolysate to one part total amino acid; this composition can further comprise ascorbic acid or ascorbate salt at a level approximately 5 parts by weight. Most importantly, it has been further found that alphaketoglutaric acid is effective in promoting development of granulation tissue by the production of collagen and can be added to starch hydrolysate or the described blends thereof at a level of approximately 1-3 parts by weight of alphaketoglutaric or salts thereof to 100 parts by weight starch hydrolysate. Table III presents the composition of a compounded starch hydrolysate blend employing particularly effective healing of pressure sores more fully described in Example 8.

TABLE III

Compounded Starch Hydrolysate Composition

| Component | Approximate Concentration in Parts by Weight/100 Parts Starch Hydrolysate |
|---|---|
| Glycine | 1 |
| L-Proline | 1 |
| L-Lysine | 1 |
| Ascorbic acid | 5 |

TABLE III-continued

Compounded Starch Hydrolysate Composition

| Component | Approximate Concentration in Parts by Weight/100 Parts Starch Hydrolysate |
|---|---|
| Alphaketoglutaric Acid | 1 |
| Fe SO$_4$ | (trace) |

Ferrous sulfate is a component in the preferred composition presented in Table III to provide Fe++ ion which is believed to promote collagen formation; other suitable ferrous salts can also be employed.

While compounded starch hydrolysate compositions similar to that presented in Table III are considered preferable, suitable compounded starch hydrolysate compositions have been prepared by slowly adding starch hydrolysate powder to multiple amino acids solutions such as that presented in Table II; after adding ascorbic acid and/or ascorbate salt as well as alphaketoglutaric acid to the solution, the solution mixture can be slowly subjected to low temperature evaporation or to freeze-drying to obtain an alternative formulation of compounded starch hydrolysate in powder form for application to wounds following thorough irrigation with buffered salt solution as more fully described in Example 9.

Further, excellent results in the treatment of wounds has been obtained by adding the components of Vitamin B complex to an amino acid solution as more fully described in Example 10. Alternatively, the dry Vitamin B complex components can be added to starch hydrolysate powder mixtures.

The compounded starch hydrolysate compositions can also be cast into films and into textile dressings such as band aids and gauze.

The following examples illustrate the use of amino acids in the treatment according to this invention but do not indicate limitation upon the scope of the claims.

EXAMPLE 5

The subject was a 65 year old uncontrolled diabetic man than suffered a severe infection of his left foot that resulted in diffusive and invasive celullitis with gangrene of the great toe and second toe. Amputation of the great toe, second toe, first and second metatarsal bones was required in order to remove all of the gangrenous parts. A large, extensive area of severe infected tissues was left following the amputation. Several tendons and bony areas were left exposed by the amputation and debridement procedure. The test area was irregular and measured 15 cms. by 8 cms. at its widest points. There were at least 3 bacterial species present. It was treated daily with irrigation with phosphate buffered salt solution pH 7.4 (Solution A—Table I) and covered with starch hydrolysate powder to which sodium ascorbate had been added on a 5 wt. % basis. The area was then covered with a non-adherent Telfa® dressing and it was further irrigated lightly with a multiple amino-acid solution (Aminosyn ™ 10%). From the first post-treatment day it was noted that the bacterial flora and purulent exudate diminished significantly. By the second post-treatment day the wound appeared free of infection and the granulation tissue and surrounding skin was seen proliferating in a rapid manner. The granulation tissue in particular appeared to be highly vascularized. The wound began to fill in from the bottom and by the 5th post-treatment day the presence of an intimately adhered pale-yellowish film was observed, covering the totality of the treated area. This newly formed film over the granulation tissue of the wound site was not adherent to the Telfa® dressing and had a very smooth shiny, textured surface. The film in question was rather thin, about 15/1000 of an inch in thickness and was intimately adherent throughout to the underlying granulation tissue, even down to the inutest crevice. The film could be sectioned and detached with fine blades and tissue forceps, but in so doing, it would tend to try to remain attached to the underlying granulation tissue capillaries with attendant hemorrhage. During the tearing-lifting process, very fine filaments and membrane like formations could be seen clinging to the granulation tissue. The surface under the film was perfectly clean and free of infection and purulent exudate.

A very interesting finding was the observation of a net-work of very small to small to medium sized arterial blood capillaries and vessels which could be seen growing under and attached to the under-surface of this newly formed in-situ biological film. This film appears to be permeable while in situ to the buffered salt solution and amino-acid solutions. Further vigorous flushing the buffered salt solution either with a large syringe with 25 gage needle, or with Water Pik, failed to tear it or to completely detach it or remove it. Further, under this in vivo formed film, the growth of a highly vasularized granulation tissue continued in an orderly and uniform way, bringing about the almost anatomical re-shaping and reconstruction of the amputated foot. It was interesting to note that the new film would come up to the skin edges and blend into the advancing epithelium in a very smooth, barely distinguishable manner. As healing would continue, the epithelium would grow and advance under the film. By the end of 6 weeks the initial defect was reduced to 7 cms. by 3 cms. In order to speed up the final recovery, and with an excellent granulation tissue base, an autologous split-thickness skin graft was applied with successful results.

EXAMPLE 6

The subject was a 34 year old paraplegic, paralyzed from the waist down following transection of the spinal cord at the level of Dorsal Vertebra #5. This accident happened as he fell from a tree where he was working as a tree-surgeon when struck by a high powdered electrical wire. For the past 4 years since the injury he has been developing multiple decubitus ulcers (pressure sores) in both hip areas, pre-sacral area and both ischitia regions. For the treatment thereof he underwent 25 plastic surgery procedures, such as autologous skin grafts and flap mobilization procedures, all of which failed shortly after surgery because of persistance of the same problem that caused the decubiti in the first place, namely, pressure and lack of circulation.

He was transferred to our service in a local hospital and was placed in a fluidized bed Clinitron and was treated daily by irrigation with phosphate buffered salt solution pH 7.4$_R$ application of starch hydrolysate with 5% ascorbic acid added, and multiple amino-acid solution (Aminosyn ™ 10%). As an example, one of the hip lesions (Trochanteric region) or pressure ulcer measured initially 8 cms. ×4 cms. with a depth of 1.7 cms. The ulcer undermined the skin edges, and these could be lifted up with the finger for about 2.5 cms. all around the ulcer. There was frofuse purulent exudate and at least 5 bacterial species were bacteriologically determined.

Within 24 hours the purulent exudate decreased significantly. The foul smelling characteristic of necrotic infected tissue also disappeared. Underlying granulation tissue befan to proliferate with abundant capillary growth. The skin edges became attached to the underlying granulation tissue and the overall size of the ulcer progressively diminished. By the fourth day, post-treatment, the presence of a thin, shiny, structured, smooth, film was observed. This film covered the totality of the ulcer granulation tissue area and blended with the epithelium at the edges. The film could be detached with a thin hypodermic needle, or it could be incised-cut with a surgical knife blade and could be lifted up with very fine tissue forceps with teeth. The film was very adherent to the underlying granulation tissue and when detached, did so, with the formation of fibers and film bands. It had an elastic consistency but was rather firm in spite of its extreme thinness (25/1000 inch). Small to medium size capillaries could be seen as a network of newly formed vascular tissue. Under the film, which was totally adhered and or bonded to the underlying granulation tissue, there were no dead spaces, real or virtual, and no serous, or purulent exudate, indicating the disappearance of infection and infectious bacteria. By the end of 6 weeks the original ulcer site was reduced to 2 cms. by 1½ cms. By the end of 8 weeks the origainl defect was completely healed and covered by newly formed epithelium, without the evidence of scar tissue, and complete anatomical reconstruction of the area.

EXAMPLE 7

The subject was a 48 year old married man that suffered 15% 2nd and 34d degree burns of the face, scalp and the dorsal and palmar aspects of both hands. He was admitted to the burn unit and treated every other day with total body immersion in special Burn Treatment Tank. The left hand was used as control and received only balanced salt solution irrigation and was wrapped in standard gauze. The face and right hand were treated daily by irrigation with phosphate buffered salt solution, 10% amino acid solution and application of starch hydrolysate with 5% sodium ascorbate. The face and head were covered with a thin, loose gauze and the hand was bandaged with loose roller bandage dressings. It was interesting to note that even 6 hours post-operatively following the treatment the face burn a yellowish, thin, pliable film had formed over the burned areas of the face treated. At 24 and 48 hours post-treatment the film was definitely formed as previously described was adherent and measured 30/1000". The burn surface was originally massively infected, but as soon as the film was formed over it, infection decreased. By the fourth day, if any pockets of exudate (pus) formed under the film, it was necessary to remove it with forceps and repeat the treatment. By the end of the 8th day, it was possible to detach most of the face film, leaving exposed a totally healed burn surface, with normal epithelium, absence of scars and no disfiguration. The burn of the right hand, being a mixture of 2nd and 3rd degree burn, took a little longer to heal by complete epithelization. By the end of the 12th treatment day, the original burn site was completely healed by newly formed epithelium without the evidence of scar. The control site, the left hand, even though it was less deep than the right hand, was not completely healed by the end of the fourth week. This treatment, directly over the the original burn eschar, formed a film envelop over all the burn area, thus providing:

a. immediate protection for further contaimination and infection b. initiation of the bactericidal/bacteriostatic effect; and c. initiation of the in situ hyper-alimentation of burned tissues.

EXAMPLE 8

This is a report on the medical case of a 28 year old housewife, paraplegic for the past 5 years following traumatic injury to her spinal chord at the level of the dorsal vertebra #2. She developed a deep, heavily infected, foul smelling decubitus ulcer on the scaral area, just above the rectal region. It measured 5.5 cms. × 1.5 cms. by 2 cms. in depth. There were 4 bacteriological species present. The lesion was treated daily by irrigation with phosphate buffered solution and then covered with starch hydrolysate powder mixed with the following amino acids: to each 100 gms. of starch powder were added glycine, 1 g.; l-proline, 1 gm. and L-Lysine 1 gm. To this mixture was added 5 gm. of sodium ascorbate, 1 gm. of alphaketoglutaric acid; and a trace of ferrous sulfate. Within 24 hours the base of the decubitus ulcer began to clean up and infection began to decrease. At 48 hours post treatment highly vascularized granulation tissue began to fill the ulcer site. Growth of granulation tissue continued and was also accompanied by centripetal growth of epithelium. By the 28th post treatment day, the ulcer site was completely healed and covered by newly formed skin without scar tissue.

EXAMPLE 9

This is the case of a 68 quadriplegic woman with a deep ischiat decubitus ulcer and a deep extensive ulceration of her left heal, of 9 years duration. The areas were treated daily with phosphate buffered salt solution and then covered with a mixture prepared as follows: to 100 cc of Aminosyn TM 10% solution, 100 grams of starch hydrolysate powder was slowly and gently added, with frequently stirring; then 5 gms. of ascorbic acid, 2 gms. of alphaketoglutaric acid approximately 0.1–0.5 gm Fe $SO_4$ were added to the mixture. The mixture was slowly subjected to a low temperature vacuum evaporation procedure at approximately 32° F. to produce a powdered mixture of all the components. One of the first observations made was that the applied powdered mixture did not seem to become diluted in the wound as readily as it did when the 10% amino-acid solution was added. The mixture was slowly wetted by the wound's own fluids (serum, etc.). There has been no local nor systemic inflammatory reaction to this new type of application. It appears that the rate of healing is faster than previously noted and that the rate of wound closure (contraction of the wound) takes place much more eadily and faster, which is believed to be due to the addition of the factors known to accelerate collagen formation in vitro, $Fe++$, $O_2$, alphaketoglutaric acid and ascorbate. By the end of 20 days both lesions were completely healed and covered by a smooth, scar free epithelium.

EXAMPLE 10

A ten month old female infant, who while receiving intravenous medication through a vein in her lower leg for a serious upper respiratory infection, suffered extravasation of the intravenous medication. This was treated with hot wet compresses and a deep third degree burn of the medical aspect of the foot and ankle ensued. It measured approximately 3×4 cms and its bottom was covered by thick eschar tissue, which was necessary to debride surgically and with proteolytic enzymes. Then, once debridement of the burn eschar was accomplished, daily treatments with phosphate buffered salt solution (solution A-Table I), starch hydrolysate powder and 10% aminoacid solution were employed. To 500 ml. of the 10% amino acid solution Aminosyn TM a solution in distilled water containing the Vitamin B components in the following proportion was added:

10 ml. contained

| | |
|---|---|
| Thiamine Hydrochloride | 250 mg. |
| Riboflavin | 50 mg. |
| Niacinamide | 1,250 mg. |
| Pyridoxine Hydrochloride | 50 mg. |
| Sodium panthothenate | 500 mg. |

The area was then covered daily with Telfa ® dressing and the procedure was repeated daily. No untoward reaction was observed to the addition of the Vit. B. complex components. The response of the granulation tissue growth was excellent, as well as the growth of the surrounding epithelium.

What is desired to secure by Letters Patent of the United States is:

1. A composition for application to skin wounds comprising, in effective amounts:
    (a) a starch hydrolysate having a Dextrose Equivalent less than about 35; and
    (b) at least one component selected from the group consisting of alphaketoglutaric acid and alphaketoglutarate salts.

2. The composition according to claim 1 comprising said alphaketoglutaric acid in the relative concentration of approximately 1–3 parts by weight alphaketoglutaric acid to one hundred parts by weight of said starch hydrolysate.

3. The composition according to claim 1, which composition further comprises at least one component selected from the group consisting of ascorbic acid and ascorbate salts.

4. The composition according to claim 1, which composition further comprises at least one ferrous salt.

5. The composition according to claim 1, 2, 3 or 4 which composition further comprises an amino acid.

6. The composition according to claim 5 wherein at least one said amino acid is selected from the group consisting of glycine, L-Proline and L-Lysine.

* * * * *